United States Patent [19]
Touhey, Jr. et al.

[11] 3,954,825
[45] May 4, 1976

[54] BIURET POLYISOCYANATES

[75] Inventors: William Joseph Touhey, Jr., Wilmington; Harry Walter Wolfe, Jr., Newark, both of Del.

[73] Assignee: E. I. Du Pont de Nemours and Company, Wilmington, Del.

[22] Filed: Apr. 5, 1974

[21] Appl. No.: 458,183

Related U.S. Application Data

[63] Continuation-in-part of Ser. No. 387,030, Aug. 9, 1973, abandoned.

[52] U.S. Cl. .................... 260/453 AB; 260/2.5 AT; 260/77.5 AT
[51] Int. Cl.² ..................................... C07C 119/042

[58] Field of Search ............................. 260/453 AB

[56] References Cited
UNITED STATES PATENTS 3,824,266  7/1974  Dietrich et al. .............. 260/453 AB

*Primary Examiner*—Lewis Gotts
*Assistant Examiner*—Dolph H. Torrence

[57] ABSTRACT

Biuret polyisocyanate is prepared by reacting a hindered polyamine and a polyisocyanate at elevated temperatures, in the presence of an excess of polyisocyanate. The resulting product may be utilized to prepare an outstanding foam composition.

4 Claims, No Drawings

BIURET POLYISOCYANATES

RELATED CASES

This case is a continuation-in-part of U.S. Ser. No. 387,030 filed Aug. 9, 1973 for William J. Touhey, Jr. and Harry W. Wolfe, Jr., now abandoned.

BACKGROUND OF THE INVENTION

This invention relates to a method for preparing biuret polyisocyanates, and in particular relates to a method for preparing biuret polyisocyanates from hindered diamines and diisocyanates.

It has been known, in the past, to form polyurethanes by reacting polyols and polyisocyanates. Foams may be produced by this reaction if it is conducted in the presence of a blowing agent.

The foams which have been formed in this manner, have in general, been satisfactory but a need for improvement in certain areas still exists. For instance, foams often are shipped in railroad box cars and because of their voluminous nature a great deal of space is needed to transport them. A foam which could be compressed during shipment and decompressed at its destination to its original size and shape would of course be an improvement since it would require less space in transit and enable one to ship greater quantities in the same transporting vehicle.

Further, quality control when preparing polyurethane foams, has been difficult because the ultimate physical properties have been slow to develop after requiring periods up to a few days for completion. Consequently, prompt recognition and rectification of problems could not be made since approximately several days were required on occasion to determine if there was in fact a problem to be solved.

Thus, a need exists for polyurethane foam which may readily be compressed for shipping and also develop ultimate properties rapidly so that quality controls procedures may be applied promptly when they are needed; the foam must not be deficient with respect to any other properties.

SUMMARY OF THE INVENTION

According to this invention a biuret polyisocyanate has been discovered which when reacted with an organic compound containing active hydrogen will form the desired polyurethane foams. It is also intended to be within the scope of the instant invention to form elastomers, coatings and adhesives by means of reactions with the same biuret polyisocyanate.

The biuret polyisocyanate, which is preferably a dibiuret, is formed by reacting a hindered polyamine, e.g. diamine, and an excess of a polyisocyanate, e.g. diisocyanate. The preferred polyamines are diamines and remarks made with respect to a diamine in this application are meant to include polyamines having three or more amine groups.

The diamine component must have amine groups which are substituted to an aromatic nucleus and are hindered by having positioned ortho thereto a fluorine, chlorine, bromine, $CF_3$, $NO_2$ or COOR (where R is $C_1$-$C_4$ alkyl) substituent. The amine component may have from 6 to 40 carbon atoms; the simplest diamine is a phenylene radical substituted with two amino groups and with a hindered substituent ortho to each amino group, 2,5-dichloro-1,4-phenylenediamine is an example of this type of compound. An especially preferred diamine is 4,4'-methylenebis-(2-chloroaniline).

The diisocyanate which is utilized may be aromatic, aliphatic or cycloaliphatic diisocyanate. The preferred organic polyisocyanates are $C_8$-$C_{25}$ aromatics, $C_2$-$C_{18}$ aliphatics and $C_5$-$C_{25}$ cycloaliphatics.

In particular, an aromatic diisocyanate, e.g., toluene diisocyanate is much preferred. This would include toluene-2,4-diisocyanate, toluene-2,6-diisocyanate and mixtures thereof.

Regarding the reaction itself, at least two moles of diisocyanate are present for each equivalent of the hindered amine group. The temperature for the reaction is elevated and should range between about 80°-200°C., preferably 130°-180°C. Pressure is preferably ambient but superatmospheric may also be utilized. The reaction will generally take place in a maximum period of about 24 hours depending on the ingredients, their concentration, the temperature and the equipment available.

The resulting biuret, if it is to be formed into a foam, is then reacted with a suitable organic compound containing active hydrogen groups as determined by the Zerewitinoff method in the presence of a blowing agent such as water or trichlorofluoromethane. Flexible foams having the desired properties which are enumerated above can be prepared in this manner.

DETAILED DESCRIPTION

This invention relates to novel biuret polyisocyanates, a method for their preparation and their use in producing superior polyurethanes, especially flexible foams.

The biurets are produced by reacting a hindered diamine and a diisocyanate. The diamine component must have amine groups which are substituted to an aromatic nucleus and are hindered by having positioned ortho thereto a fluorine, chlorine, bromine, $CF_3$, $NO_2$ or COOR (where R is $C_1$-$C_4$ alkyl) substituent. The diamine can vary widely and may contain 6–40 carbon atoms, typically between about 6-20. As mentioned previously the simplest diamine is a phenylene radical substituted with two amine groups and with a hindered substituent ortho to each amino group; 2,5-dichloro-1,4-phenylene diamine is an example of this type compound. In general compounds having two phenyl radicals, each having an ortho substituted amino group are more readily accessible. The compounds may be represented by the general formula:

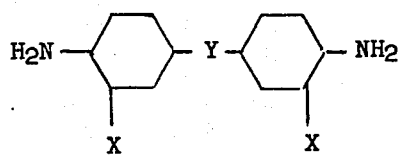

wherein X is hindering group such as hereinbefore named and —Y— is a biradical of which —$CH_2$—, —O—, —S—, —S—S—,

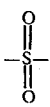

lower alkylene and phenylene radicals are exemplary. Y may also be omitted so that the phenyl radicals are joined together to yield a biphenyl derivative.

In the general formula, the amino groups are shown in the para positions and while compounds having this structure are generally most readily available, the amino groups may also be positioned ortho or meta to the bond of the biradical connecting the phenyl radicals. It is not necessary that the molecule be symmetrical with reference to the positions occupied by the amino groups or the nature of the ortho substituents. The following compounds are representative of diamines of this type: 4,4'-methylenebis-(2-fluoroaniline), 3,3'-dichlorobenzidine, 4,4'-diamino-3,3'-dichlorodiphenyl ether, 4,4'-diamino-3,3'-dichlorodiphenylsulfide, 4,4'-diamino-3-chloro-3'-bromodiphenylmethane, 4,4'-methylenebis(2-carbonethoxyaniline), 4,4'-methylenebis(2-trifluoromethyl aniline) and 3,3',5-trichloro-4,4'-diaminodiphenylmethane. Of these compounds, 4,4'-methylenebis(2-chloroaniline) is preferred.

Of the diamines having two phenyl radicals, derivatives of methylene dianiline are a preferred class. These diamines are readily prepared by condensation of properly substituted aniline derivatives with formaldehyde in the presence of strong acids. The crude condensates obtained by this reaction can be used directly after any excess aniline derivatives have been removed. In carrying out the condensation from about 1.0 to 10 moles of substituted aniline per mole of formaldehyde can be used. If less than about 3 moles of aniline are used per mole of formaldehyde, significant amounts of polyamines having functionalities of three or more are obtained in addition to the diamine. Such products are useful in the present invention. Suitable aniline derivatives include o-chloraniline, o-nitroaniline, o-trifluoromethylaniline and o-carbomethoxyaniline. These may be used alone or in admixture in carrying the condensation. Condensation products in which a portion of the ortho-substituted aniline is replaced by aniline itself or an unhindered aniline derivative such as meta-toluidine can also be used in the present invention as long as at least 50% of the amine groups in the condensation product are hindered by fluorine, chlorine, bromine, —CF$_3$, — NO$_2$ or COOR wherein R is C$_1$-C$_4$ alkyl. A preferred product of this type is prepared by condensing a mixture of o-chloroaniline and aniline (about 2 to 4 moles of o-chloroaniline per mole of aniline) with formaldehyde using 1.3 to 2.0 moles of total amines per mole of formaldehyde. U.S. Pat. No. 3,563,906 to Hoeschele includes a detailed description of the preparation of such mixed amine condensation products and its disclosure is hereby included by reference.

Other substituents may be present on the aromatic nucleus or nuclei as long as they are inert toward isocyanate and amino groups. Representative of additional substituents which may be present are alkyl, aryl, alkoxy, aryloxy and alkenyl groups. More than one substituent selected from the group represented by X may also be present as long as at least one of them is ortho to the amino group. Diamines based on fused carbocyclic ring structures in which at least one ring is aromatic and in which two hindered aromatic amine groups are present can also be used. The following are representative of this type of diamines which can be used in the present compositions:

2,6-dichloro-1,5-diaminonaphthalene
2,3-dichloro-1,4-diaminonaphthalene
5,6-dichloro-4,7-diaminobenzofuran Polyisocyanates are reacted with the diamine component to form the biuret polyisocyanate. Again, the description will be made in terms of diisocyanates; however, it is to be emphasized that they are merely illustrative of polyisocyanates and polyisocyanates containing 3 or more isocyanate groups are intended to be included as well as the diisocyanates. Broadly, the organic diisocyanates which are to be utilized may be defined as aromatic diisocyanates containing 8–25 carbons, aliphatic diisocyanates containing 2–18 carbons and cycloaliphatics containing 5–25 carbon atoms. Specifically, aliphatic diisocyanates and cycloaliphatic diisocyanates which are preferred include 1,4-tetramethylene diisocyanate, 1,6-hexamethylene diisocyanate, 1,3- and 1,4-cyclohexyldiisocyanates, methylene-bis(4-cyclohexyl diisocyanate), 1,3- and 1,4-xylene diisocyanates. Of these, 1,6-hexamethylenediisocyanate and methylenebis(4-cyclohexyl diisocyanate) are preferred.

The aromatic diisocyanates are preferred. Representative of these diisocyanates are tolylene-2,4-diisocyanate, tolylene-2,6-diisocyanate and mixtures thereof such as those mixtures containing at least 50% of the 2,4-isomer. Other representative aromatic diisocyanates include 4,4'-methylenebis(phenyl isocyanate), 1,3- and 1,4-phenylene diisocyanate, 2,4-bis(4-isocyanatobenzyl)-phenylisocyanate and related polyaryl polyisocyanates, 1,5-naphthalene diisocyanate and mixtures thereof. The diisocyanates may be substituted with alkyl, alkoxy, halogen, nitro, or carboalkoxy groups. The 2,4- and 2,6-tolylene diisocyanates are especially preferred. 4,4'-methylenebis(phenyl isocyanate) is also preferred.

All of the above isocyanates can be employed in either refined or crude (undistilled) form.

Concerning the ratio of the reactants, at least two moles of polyisocyanate are utilized per equivalent of hindered amine group, preferably between 3-20 moles of diisocyanate are utilized per equivalent of hindered amine group.

The reaction may take place at a temperature between about 80°–200°C, preferably between about 130°–180°C. The reaction is normally run at ambient pressure but pressure can be employed if required because of the presence of low boiling intermediates or solvents. Ambient pressure is much preferred. The use of elevated temperature is, however, critical since it appears that in this manner the insoluble diurea which is initially formed is converted to the soluble dibiuret. It should be emphasized that this is theoretical and there is no intention to be bound by any theory.

It is difficult to be precise regarding the time required for completing the reaction since the reaction speed will vary with the type of equipment being employed and the temperature utilized as well as the particular starting materials and their concentration. In batch reactions, usually 1–24 hours are required. Reaction times of less than an hour can be achieved in continuous reactors. The progress of the reaction can be followed by measuring the isocyanate group content of the reaction mass. Two equivalents of isocyanate group react with an equivalent of amine.

Solvents can be employed if desired in carrying out the reaction. The solvents must of course be inert toward isocyanate and amine groups. In addition, if low boiling solvents are used it may be necessary to use pressure reactors at the temperatures required to complete the reaction. Suitable solvents include benzene, xylene, o-dichloro benzene, 1,2,5-trichlorobenzene, diethyleneglycol dimethyl ether and dibutyl phthalate to name a few.

The biuret polyisocyanates are normally obtained as solutions or slurries in the excess diisocyanate which was used in their preparation. They may be used as such or may be isolated by filtration. They may be precipitated from their solutions by addition of aliphatic hydrocarbons such as hexane and obtained by filtration. It is particularly convenient to prepare the biuret polyisocyanates in the presence of a sufficient excess of diisocyanate such that a solution of biuret polyisocyanate which is stable at room temperature is obtained. Such solutions are particularly useful for preparing foams and elastomers. In the case of 4,4'-methylenebis(2-chloroaniline) and tolylene diisocyanate stable solutions containing up to about 25% biuret polyisocyanate can be prepared.

The biuret polyisocyanates are low molecular weight materials which yield solutions having low viscosity and no visible solids. They are nearly colorless or pale amber when prepared from refined diamines and diisocyanates. This is surprising in view of prior art indicating that diamines in general when reacted with diisocyanates yield unsatisfactory products.

The resulting biuret polyisocyanate may be used to form polyurethanes and other isocyanate reaction products by reacting it with organic compounds containing active hydrogen as determined by the Zerewitinoff method. Any suitable organic compound containing at least two active hydrogen containing groups may be used. Generally speaking, compounds containing alcoholic groups are strongly preferred because they are readily available and yield stronger urethane linkages than do phenolic type hydroxyl group. In addition, compounds containing $NH_2$, NH, COOH, SH groups and the like may be utilized to form the various known types of isocyanate reaction products. Examples of suitable types of organic compounds containing at least two active hydrogen containing groups which are reactive with an isocyanate group are polyesters, polyols, polyhydric polyalkylene ethers, polyhydric polythioethers, polyacetals, aliphatic polyols including alkane, alkene and alkyne diols, triols, tetrols and the like, aliphatic thiols including alkane, alkene and alkyne thiols having two or more -SH groups; polyamines containing both aromatic, aliphatic and hetrocyclic diamines, triamines, tetramines and the like; as well as mixtures thereof. Listings of compounds which fall within these various categories may be found in U.S. Pat. No. 3,201,372, the disclosure of which is herein incorporated by reference.

A preferred reaction of the biuret polyisocyanates, particularly in the form of their solutions in additional isocyanate, is that with polyether polyols or polyester polyols containing 2–8 hydroxyl groups and having equivalent weights of about 100 to 3000 in the presence of an expanding agent to form rigid, semi-rigid and flexible foams. Prepolymer, semi-prepolymer and one-shot precedures can be used for foam preparation. Generally, the one-shot procedure is preferred.

An especially preferred reaction of the biuret polyisocyanates in the instant invention is that with a high molecular weight polyether polyol in the presence of a blowing agent to form a flexible polyurethane foam. The polyols preferably have number average molecular weights of from about 3,000–8,000, most preferably from about 4,000–6,500. The preferred polymeric polyols are polyalkylene ether glycols or triols or mixtures thereof. Polyether polyols of this type can be obtained by reaction of an alkylene oxide, for example, ethylene oxide, propylene oxide, etc., with a polyhydric alcohol such as ethylene glycol, propylene glycol, dipropylene glycol, glycerol, trimethylolpropane or mixtures thereof. Activated or balanced polyols can also be used. Activated polyols are prepared from a mixture of alkylene oxides such as ethylene oxide and propylene oxide, and balanced polyols are prepared by separately reacting different alkylene oxides so that a block copolymer containing two or more different poly(oxyalkylene) blocks is obtained. Balanced polyols in which the terminal blocks are derived from ethylene oxide are especially preferred as are polyols capped with limited amounts of ethylene oxide. Such polyols contain at least some primary hydroxyl groups which increase the reactivity of the polyol.

The blowing agent which is to be employed to expand these preferred formulations of this invention to a foam during the reaction of the polyol and the biuret polyisocyanate is utilized by techniques well known in the art. Suitable blowing agents are water and halogenated hydrocarbons such as trichlorofluoromethane and methylenechloride. The density of the foam can be varied by using different proportions of the blowing agent. The preferred blowing agent is water because of its convenience and availability. In general, about 2–5 parts by weight of water per 100 parts of polyol are used. However, greater or lesser amounts can be employed depending upon the density of the foam desired.

Catalysts are normally used to promote the isocyanate-polyol reaction and the water-isocyanate reaction when water is the blowing agent. Conventional type catalysts can be used such as tertiary amines and the usual organo-tin catalysts such as dibutyltin dilaurate and stannous octoate. The catalyst is generally used in the amount of about 0.01–2.0 parts per 100 parts of polymeric polyol.

Other materials which can be employed in the production of the foams of this invention at the discretion of one skilled in the art include stabilizers, pigments, fillers, flame retardants and extenders.

A typical stabilizer would be, for example, sulfonated castor oil and silicones such as polydimethylsiloxanes. On occasion it may be desirable to employ silicones of the block copolymer in minor amounts.

Outstanding HR (high resilience) foams can be prepared from the capped polyols of 3,000–8,000 molecular weight described hereinbefore using a solution in excess toluene diisocyanate of the biuret polyisocyanate derived from 4,4'-methylenebis(2-chloroaniline) and toluene diisocyanate with water as a blowing agent. No added crosslinking agent such as a low molecular weight polyamine or polyol is required to achieve hardness and rapid demolding using this system.

The flexible polyurethane foams of this invention can be produced either in slab stock or in a specifically molded configuration; thus they can be used as a seating material in furniture or automobiles. Other automotive applications such as head rests, instrument panels and elastomeric bumpers form an important outlet for these foams.

If it is desired to prepare rigid foams from the biuret polyisocyanate compositions of this invention polyether polyols having higher functionality obtained by oxypropylating polyols should be utilized. Such polyols include sucrose, sorbitol, glycerin, trimethylol propane, 1,2,6-hexanetriol, pentaerythritol, or mixtures thereof. Such polyols usually have equivalent weights of about 100–140. When rigid foams are prepared the blowing agent which is most preferred is Freon. Optionally, one may utilize the carbon dioxide gas formed in situ by the reaction of water and isocyanate. A detailed discussion of the materials and techniques which can be used in the preparation of polyurethane rigid foams using the isocyanates of this invention can be found in "High Polymers", Saunders and Frisch, Vol XVI, Polyurethanes: *Chemistry and Technology*, Interscience Publishers, New York, Chapter VIII, entitled "Rigid Foams". The above mentioned chapter is herein incorporated by reference.

Important uses of the rigid foams of this invention include refrigeration insulation and flotation in marine applications.

The biuret polyisocyanates of this invention are also useful in preparing polyurethane elastomers. Isocyanate terminated prepolymers can be readily prepared from polyether or polyester glycols having molecular weights of about 300–3,000 and solutions of buiret polyisocyanates in diisocyanates. The resulting prepolymers can be cured to useful elastomers with curing agents such as low molecular weight polyols or polyamines. Illustrative curing agents include 1,4-butanediol trimethylol propane, methylenebis(2-chloroaniline) and methylene dianiline. A detailed discussion of materials and techniques for polyurethane elastomers can be found in "High Polymers", Saunders and Frisch, Vol. XVI, Polyurethanes, Chemistry and Technology, Part II, Interscience Publishers, New York, Chapter IX, entitled "Elastomers". The above mentioned chapter is herein incorporated by reference.

Coatings can also be prepared from the biuret polyisocyanates, either in the form of its solution in excess isocyanate or a solution in an organic solvent, or as the isolated solid, the latter being of course free of any free diisocyanate. Both one-part moisture cure coatings and two-part coatings can be prepared by conventional techniques. Handling of the pure biuret can be simplified by dissolving it in an inert solvent. Chapter X of Saunders and Frisch which was cited hereinbefore contains detailed procedures for coating preparation. This chapter is herein incorporated by reference.

The invention is further illustrated by the following examples wherein parts and percentages are by weight unless otherwise indicated.

EXAMPLE 1

Preparation of Biuret Polyisocyanate

A. To 2940 grams of 2,4-tolylene diisocyanate heated to 110°C., 218 grams of molten 4,4'-methylenebis(2-chloroaniline) is added over a period of 30 seconds, with agitation. A precipitate of the diurea is observed to form within about 10 seconds after the addition of the diamine is commenced. This diurea disappears as the resulting exotherm elevates the reaction medium to 140°–150°C. At this level, the diurea is converted to a dibiuret that is soluble in the excess tolylene diisocyanate.

After all of the solid material has disappeared, in about 30 minutes, the reaction mass is cooled to ambient temperature. The isocyanate content of the reacted mass is 40.05%. The viscosity at 23°C. is 29 cps.

B. Substantially identical results are obtained when the 2,4-tolylene diisocyanate is replaced by an equal weight of an isomer mixture of 65% 2,4- and 35% 2,6-tolylene diisocyanate.

EXAMPLE 2

A high resilience foam is prepared by continuously mixing the following mixtures as separate streams in a commercially available foam machine.

| Stream 1 (Temperature ~27°C.) | 38.4 parts |
|---|---|
| Biuret Polyisocyanate prepared in Example 1B | |
| Stream 2 (Temperature ~27°C.) | |
| Polyoxypropylene ether triol based on trimethyol propane, capped with ethylene oxide, ratio of ethylene oxide/propylene oxide 12/88 to 15/85, number average molecular weight about 4700 | 100 parts |
| Water | 2.7 parts |
| Polydimethylsiloxane oil - 5 centistoke grade | 0.02 part |
| Triethylene diamine | 0.13 part |

Material leaving the foam mixing machine is introduced into a 15 × 15 × 4½inches aluminum mold and the mold is closed so that foaming takes place under the pressure developed during foaming. The foam is removed from the mold after 8–10 minutes and passed through rolls to break any closed cells. The foam is then cured for 30 minutes at 120°C. and conditioned for 3 days at about 25°C. prior to testing.

Typical properties obtained from this foam by ASTM D-1564 methods are as follows:

| Density, lb./cu.ft. | 2.6 |
|---|---|
| Tensile at break, psi | 20 |
| Elongation at break, % | 165 |
| Split tear, pli | 1.5 |
| 50% comp. set after humid age 5 hrs, 121°C., 100% R.H. | 18 |
| 75% comp. set, % | 7 |
| ILD at 65% defl., lbs. | 76 |

Not shown in the above data is the excellent compression packaging character of the foams which is obtained within 30 minutes after removal from the post cure oven. The test consists of placing the molded foams, 15 × 15 × 4½ inches in a V-shaped clamp that compresses the foam at one edge at 0% and at the opposite edge, 70%. The clamp with the foam compressed, is held 22 hours at 70°C. after which the foam is released. After standing 30 min. at ambient temperatures the recovery of height of the compressed edge is in excess of 85%.

EXAMPLE 3

To 262 grams of the biuret polyisocyanate (prepared in Example 1A) 600 grams of polytetramethylene ether glycol, MW 1000, are added with agitation. The reaction mass is allowed to exotherm, for about 30 minutes, and then it is heated to 80°C. and held at this level for 1 hour. After completion of this heating cycle, the reaction mass is cooled to ambient temperatures. The NCO content of the prepolymer is about 6.2% while the viscosity at 250°C. is about 26,000 cps.

To 100 parts of this prepolymer heated to 85°C. is added a mixture of 5.06 parts of 1,4-butanediol, 1.26 parts of trimethylol propane and 0.015 part of stannous octoate. After mixing vigorously, the material is poured into compression molds to form 75 mil thick slabs for testing. The slabs are cured for 20 hrs./100°C. and aged for a week at 50% relative humidity at 25°C. before testing.

The following properties are observed.

| | |
|---|---|
| Modulus at 100% elongation, psi | 300 |
| Modulus at 300% elongation, psi | 1000 |
| Tensile at Break, psi | 2200 |
| Elongation at Break, % | 350 |
| Hardness, Shore A (ASTM D 676) | 59 |

The stress-strain properties are determined by ASTM D-412.

EXAMPLE 4

A polyamine is prepared by adding 186.5 parts of 37% aqueous formaldehyde to a slurry of 382.5 parts orthochloroaniline, 93 parts of aniline, 445 parts of 97% sulfuric acid and 650 parts of water at 50°C. Within 30 minutes, the temperature is raised to 85°C where it is maintained for 1 hour. The mass is then neutralized with 52.6% sodium hydroxide solution. The organic phase is separated and washed with hot water. The resulting polyamine is dried by distillation at reduced pressure.

Part A of Example 1 is repeated using 238 grams of the above polyamine in place of the 218 grams of 4,4'-methylenebis(2-chloroaniline) and replacing 2,4-tolylene diisocyanate with an equal weight of an 80/20 mixture of 2,4-/2,6-tolylene diisocyanate. The resulting product has an NCO assay of 40.1% by weight. This product is used to prepare a high resilience foam by the following procedure.

The following streams are mixed continuously in a commercially available foam machine.

| | | |
|---|---|---|
| Stream 1 (Temperature ~27°C) | | |
| Polyisocyanate prepared in this example | 40.6 | parts |
| Stream 2 (Temperature ~27°C) | | |
| Polyoxypropylene triol based on trimethylol propane, capped with ethylene oxide, ratio of ethylene oxide to propylene oxide 12/88 to 15/85, number average molecular weight about 4700 | 80 | parts |
| Graft polymer/polyol (hydroxyl number about 28) containing about 20% by weight graft polymer and 80% by weight polyol, prepared by copolymerizing acrylonitrile and styrene in a polyether triol having a molecular weight of about 5000 | 20 | parts |
| Polydimethylsiloxane oil - 5 centistoke grade | 0.01 | part |
| Dibutyltin dilaurate | 0.005 | part |
| Water | 2.8 | parts |
| Triethylene diamine dissolved in 2 parts of dipropylene glycol | 0.4 | part |
| Bis(N,N-dimethylaminoethyl) ether | 0.4 | part |

Material leaving the foam mixing machine is introduced into a 15 × 15 × 4½ inch aluminum mold and the mold is closed so that foaming takes place under the pressure developed during foaming. The foam is removed from the mold after 8–10 minutes and passed through rolls to break any closed cells. The foam is then cured for 30 minutes at 120°C and conditioned for 3 days at about 25°C prior to testing.

Typical properties obtained from this foam by ASTM D-1564 methods are as follows:

| | |
|---|---|
| Overall Density, lb./cu.ft. | 2.8 |
| Core Density, lb./cu.ft. | 2.4 |
| Tensile at break, psi | 15 |
| Elongation at break, % | 120 |
| Split tear, pli | 1.2 |
| 50% comp. set after humid age 5 hrs., 121°C, 100% R.H. | 28 |
| 90% comp. set, % | 6 |
| ILD at 65% defl., lbs. | 103 |

What is claimed is:

1. In a process for preparing a biuret polyisocyanate by reacting a polyamine and an excess of a polyisocyanate at a temperature of about 80-200°C. in the absence of a solvent, the improvement comprising employing a mixture of polyamines containing hindered and unhindered amine groups prepared by condensing aniline, 2-chloroaniline, and formaldehyde; the mole ratio of 2-chloroaniline to aniline being 2:1 to 4:1 and the total moles of amine per mole of formaldehyde being 1.3 to 2.0.

2. The process of claim 1 wherein said polyisocyanate is a member selected from the group consisting of a $C_8$-$C_{25}$ aromatic, a $C_2$-$C_{18}$ aliphatic, and a $C_5$-$C_{25}$ cycloaliphatic diisocyanate.

3. The process of claim 1 wherein said polyisocyanate is toluene diisocyanate.

4. The process of claim 1 wherein said polyisocyanate is a mixture of 2,4-tolylene diisocyanate and up to 50% 2,6-tolylene diisocyanate.

* * * * *